United States Patent

Smets et al.

[11] 4,113,734
[45] Sep. 12, 1978

[54] MASKED ISOCYANATES

[75] Inventors: Georges Joseph Smets, Heverlee; Jean Marie Vandensavel, Tienen, both of Belgium

[73] Assignee: Agfa-Gevaert, N.V., Mortsel, Belgium

[21] Appl. No.: 406,350

[22] Filed: Oct. 15, 1973

Related U.S. Application Data

[62] Division of Ser. No. 257,235, May 26, 1972, Pat. No. 3,790,377.

[30] Foreign Application Priority Data

Jun. 2, 1971 [GB] United Kingdom ............... 18691/71

[51] Int. Cl.² .......................................... C07D 257/06
[52] U.S. Cl. ............................................... 260/308 D
[58] Field of Search ................................... 260/308 D

[56] References Cited

PUBLICATIONS

Elderfield, Heterocyclic compounds, vol. 8, (New York, 1967), pp. 11-19.
Richter's Organic Chemistry, vol. 1, pp. 202, 204, Nordemann Publishing Company, Amsterdam-New York, (1934).
Degering, An Outline of Organic Nitrogen Compounds, pp. 267, 268, University Lithoprinters, Ypsilanti, Mich., (1945).

*Primary Examiner*—Alton D. Rollins
*Attorney, Agent, or Firm*—A. W. Breiner

[57] ABSTRACT

Masked isocyanates in which the isocyanate group or groups may be generated by heating above 100° C are formed by tetrazolinones and bis(tetrazolinones) corresponding to the formula:

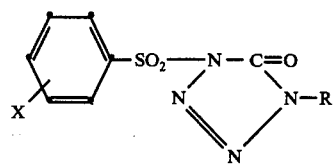

wherein X is hydrogen, halogen, nitro, alkyl (1–4 C) or a group of formula:

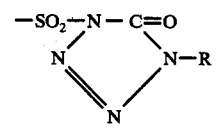

and R is an aliphatic, aromatic or araliphatic hydrocarbon radical.

The bis(tetrazolinones) may be utilized to crosslink upon heating polymers containing active hydrogen atoms. The heating may occur image-wise or record-wise so that layers composed of mixtures of polymers and bis(tetrazolinones) can be used as heat-sensitive recording materials.

2 Claims, No Drawings

MASKED ISOCYANATES

This is a division of application Ser. No. 257,235 filed May 26, 1972, now U.S. Pat. No. 3,790,377.

The invention relates to masked isocyanates and di-isocyanates, to a process for the manufacture of masked isocyanates and di-isocyanates, and to the modification of polymers using these masked isocyanates and di-isocyanates.

By masked isocyanates and di-isocyanates are meant compounds, in which the isocyanate group or groups may be generated usually by heating between 100° and 200° C.

The reactivity of the isocyanate group with compounds containing active hydrogen atoms is known. In some chemical reactions the reactivity of the isocyanate groups with compounds containing hydrogen atoms is far too high. For example, this is the case when an isocyanate or di-isocyanate is used to cure polymeric products. The polymer is cured generally before a useful commercial product can be made from this polymer.

An object of the invention is the preparation of masked isocyanates and di-isocyanates, the isocyanate groups of which can be set free by heating at relatively high temperatures. Compositions containing these masked isocyanates or di-isocyanates show the important advantage that they can be kept indefinitely at room temperature.

According to the invention masked isocyanates are provided, which correspond to the general formula:

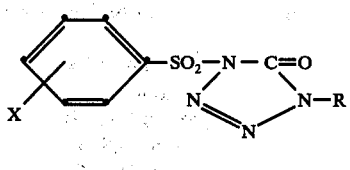

wherein:
X represents a hydrogen atom, a halogen atom, a nitro group, an alkyl group of 1 to 4 carbon atoms, or a group of the formula:

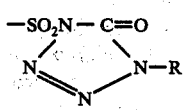

and R represents an aliphatic, aromatic or araliphatic hydrocarbon radical.

These masked isocyanates are tetrazolinones. They are prepared according to a process comprising heating in a common solvent stoichiometric quantities of an azide-substituted aliphatic, aromatic or araliphatic hydrocarbon and benzene mono- or di-(sulphonyl isocyanate the benzene nucleus of which may be substituted with a halogen atom, a nitro group, or an alkyl group of 1 to 4 carbon atoms.

Common solvents for both the isocyanate and the azide-substituted aliphatic, aromatic or araliphatic hydrocarbon are non-polar organic solvents such as carbon tetrachloride and toluene.

Representative tetrazolinones are e.g.:
1-phenylsulphonyl-4-n-butyl-2-tetrazolin-5-one
1-phenylsulphonyl-4-ethyl-2-tetrazolin-5-one
1-phenylsulphonyl-4-phenyl-2-tetrazolin-5-one
1-phenylsulphonyl-4(2'-phenylethyl)-2-tetrazolin-5-one
1-phenylsulphonyl-4(4'-phenyl-n-butyl)-2-tetrazolin-5-one
1-(p-chlorophenylsulphonyl)-4-n-butyl-2-tetrazolin-5-one
1-(p-methylphenylsulphonyl)-4-n-butyl-2-tetrazolin-5-one
1-(p-nitrophenylsulphonyl)-4-n-butyl-2-tetrazolin-5-one
1-(m-nitrophenylsulphonyl)-4-n-butyl-2-tetrazolin-5-one
1,1'-(m-phenylene-disulphonyl)-bis(4-n-butyl-2-tetrazolin-5-one)

By heating at an elevated temperature, preferably about 100° C these tetrazolinones are decomposed, so that the isocyanate group or groups are set free again. The free isocyanate groups are capable of entering into reaction with compounds containing active hydrogen atoms such as present in hydroxyl groups, amino groups, mercapto groups, lactam groups, and imide groups. Accordingly, by heating above 100° C the tetrazolinones are capable of modifying polymers containing groups with reactive hydrogen atoms. In the case of bis(tetrazolinones) the decomposition by heating of the compounds of the invention containing masked isocyanate groups may especially be utilized to cure or cross-link polymers containing active hydrogen atoms such as present in free hydroxyl or amino substituents on polymeric chains. When a bis(tetrazolinone) according to the invention is mixed intimately with a polymer containing e.g. free hydroxyl or amino groups and when the mixture is then heated above 100° C, a cross-linked, completely insoluble polymer is formed.

If this heating at elevated temperatures is executed image-wise or record-wise on a layer formed from the mixture of polymer containing free hydroxyl or amino groups and of bis-tetrazolinone according to the invention, cross-linking of the polymer only occurs at the places struck by heat and an image-wise or record-wise differentiation in the solubility or in the melt temperature of the polymer layer may be obtained. In this way the layer composed of the mixture of polymer and tetrazolinone can be used as a heat-sensitive recording material.

The heat needed to decompose the tetrazolinones of the invention image-wise or record-wise and to cross-link the polymeric binding agent at these places, can be supplied by infra-red radiation, e.g. by an infra-red laser. For instance, an original containing infra-red light-absorbing image areas may be exposed to infra-red radiation while being in heat-conductive contact with a layer containing a mixture of polymer and tetrazolinones of the invention. At the places corresponding with the image areas of the original, the layer reaches a temperature, at which the tetrazolinones are decomposed. The isocyanates thus formed react with the active hydrogen atoms of the polymer and cross-link the polymer to the insoluble state. When a finely divided substance absorbing visible light and converting it into heat e.g. finely divided carbon black, is mixed throughout a layer, which is composed of a mixture of polymer and tetrazolinone, the image-wise or record-wise decomposition of the tetrazolinones may be obtained by exposure of the layer to flashlight, more particularly to flashlight emitted by gas discharge lamps, e.g. xenon gas discharge lamps. These lamps can supply an energy of 300–1000 watt.sec. in a period of $10^{-4}$ to $10^{-2}$ seconds.

During the exposure through an original the finely divided substance absorbs visible light and converts it into heat at the places corresponding with the transparent areas of the original. As a result of this conversion into heat the tetrazolinone is decomposed in these places and the polymer is cross-linked. At the non-exposed and consequently unhardened areas the polymer can now be washed away, or these unhardened areas can be transferred by pressing against a receiving material whilst heating. This transfer can be performed as a result of the reduced solubility of the exposed and consequently cross-linked parts and of the enhanced melting temperature of these hardened parts.

As a result of the image-wise or record-wise heating at elevated temperatures of the layer formed from a mixture of polymer containing active hydrogen atoms and of bis-tetrazolinones according to the invention, a differentiation in the solubility or in the melt temperature of different areas of the layer is obtained. The areas of the layer, that have not been cross-linked by heat may be washed away with a solvent for the unmodified polymer. In this way a negative relief image of the original is formed, which may be used as a negative printing plate.

When, however, the unhardened areas are transferred by pressing against a receiving material whilst heating, a positive relief image of the original is formed. This relief image can be used as a positive printing plate after thorough hardening of the transferred areas of the layer, if needed, by heating to the decomposition temperature of the bis-tetrazolinone.

In the manufacture according to the invention of tetrazolinones containing masked isocyanate groups, it might be interesting to replace the mono-azide-substituted aliphatic, aromatic or araliphatic hydrocarbon by corresponding di- or poly-azides. As a result of the reaction with benzene mono- or di(sulphonyl isocyanates) bis- and poly-tetrazolinones are formed that contain also masked isocyanate groups. These bis- and poly-tetrazolinones are also decomposed by heat whereby the isocyanate groups are set free. Moreover, if a polymer containing azide side-substituents is reacted with the sulphonyl isocyanates, a polymer is formed containing tetrazolinon side-substituents. In fact a polymer is obtained carrying masked isocyanate groups distributed over its polymer chain, which masked isocyanate groups can be set free again by heating the polymer at a temperature above 100° C.

The synthesis of the azide-substituted aliphatic, aromatic or araliphatic hydrocarbons needed in the manufacture of the tetrazolinones of the invention is illustrated by the synthesis of n-butylazide. This n-butylazide is prepared by addition of an equimolar amount of n-butylbromide to sodium azide suspended in dimethyformamide.

The different arylsulphonyl isocyanates are synthetized by phosgenation of the corresponding sulphonamides. The sulphonamide is dissolved in chlorobenzene (o-dichlorobenzene in the case of nitro-derivatives), whereupon the water present is distilled off azeotropically. Subsequently, a catalytical amount of n-butyl isocyanate is added. Phosgene is condensed first in a slight excess, e.g. in a mixture of isopropanol and solid carbon dioxide. It is then allowed to bubble through a solution of the amide whilst refluxing. The excess of phosgene is eliminated by allowing nitrogen to bubble through the solution. The solvent and the n-butyl isocyanate are distilled off under reduced pressure, whereupon a high yield of the arylsulphonyl isocyanate is obtained by vacuum distillation.

EXAMPLE 1

Stoichiometric amounts of n-butylazide and phenylsulphonyl isocyanate dissolved in carbon tetrachloride were brought at room temperature in a carefully dried flask. The reaction course was followed by infrared spectroscopy. The slow disappearance of the azide band at 2100 cm$^{-1}$ and of the isocyanate band at 2240 cm$^{-1}$ was observed. A broad peak at 1750 cm$^{-1}$ was attributed to the $>$C$=$O absorption whereas the SO$_2$ absorptions shift, i.e.

$v_{as}$ SO$_2$ from 1380 cm$^{-1}$ towards 1400 cm$^{-1}$, and
$v_{as}$ SO$_2$ from 1185 cm$^{-1}$ towards 1200 cm$^{-1}$.

After complete reaction the solvent was distilled off under reduced pressure at room temperature. Subsequently, the residue was dissolved in ether and cooled down to −25° C, whereas the reaction product crystalized out.

The resulting 1-phenylsulphonyl-4-n-butyl-2-tetrazolinon-5-one was a white powder melting at 42.5°–43.5° C. A clear transparent crystalline powder was obtained by slow crystallization from ether. The powder corresponded to the following formula:

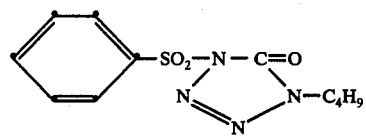

The following results were obtained by elementary analysis:

C: calculated 46.79%; found 46.80%
H: calculated 5.01%; found 4.95%
N: calculated 19.85%; found 20.05%
0: calculated 17.00%; found 16.85%
S: calculated 11.35%; found 11.35%

EXAMPLE 2

Equimolar mixtures of (p-chlorophenyl)-sulphonyl isocyanate and n-butylazide were dissolved at room temperature in toluene with a molar concentration of 0.6. 1-(p-chlorophenylsulphonyl)-4-n-butyl-2-tetrazolin-5-one was obtained, which was a white powder or a clear crystalline precipitate, according to whether the precipitation occurred fast or slow. The product had a melting range of 76.5°–77.5° C. The following results were obtained by elementary analysis:

C: calculated 41.70%; found: 41.46%
H: calculated 4.15%; found: 4.15%
N: calculated 17.69%; found: 7.52%
O: calculated 15.15%; found: 15.42%
Cl: calculated 11.19%; found: 11.18%
S: calculated 10.12%; found: 9.68%

By infrared spectroscopy the most characteristic peak was found to be a large absorption band at 1753 cm$^{-1}$, which was attributed to the $>$C$=$O absorption. The other absorptions were analogous to those described in example 1, with the difference, however, that a para-substituted product was concerned here, which gave rise to a strong absorption at 832 cm$^{-1}$.

EXAMPLE 3

Equimolar amounts of n-butylazide and (p-methylphenyl)-sulphonyl isocyanate were dissolved at room temperature in toluene with a molar concentration of 0.6. The resulting 1-(p-methylphenyl-sulphonyl)-4-n-butyl-2-tetrazolin-5-one was a white powder (or clear crystals in the case of a slow crystallization) melting at 45°-46° C.

The infrared-spectrum showed a large absorption band at 1745 cm$^{-1}$ due to the >C=O group whereas the further spectrum was analogous to that of example 1.

EXAMPLE 4

Equimolar amounts of (p-nitrophenyl)-sulphonyl isocyanate and n-butylazide were dissolved at room temperature in toluene with a molar concentration of 0.6.

In the IR-spectrum a large band due to the >C=O group was found at 1750 cm$^{-1}$.

The light yellow crystals of 1-(p-nitrophenylsulphonyl)-4-n-butyl-2-tetrazolin-5-one melted between 124° and 125° C.

EXAMPLE 5

Equimolar amounts of (m-nitrophenyl)-sulphonyl isocyanate and n-butylazide were dissolved at room temperature in toluene with a molar concentration at 0.6.

The light yellow crystals of 1-(m-nitrophenyl-sulphonyl)-4-n-butyl-2-tetrazolin-5-one melted at 90° C. In the IR-spectrum an absorption band due to the >C=O group was found at 1758 cm$^{-1}$, whereas the further spectrum was identical with that of example 4, except for the phenyl substitution (meta-substitution instead of para).

EXAMPLE 6

1 mole of m-benzene disulphonyl isocyanate and 2 moles of n-butylazide were dissolved at room temperature in carbon tetrachloride. A product melting at 124° C was formed. In the IR-spectrum an absorption band due to the >C=O group was found at 1755 cm$^{-1}$. 1,1'-(m-phenylene-disulphonyl)-bis(4n-butyl-2-tetrazolin-5-one) was obtained.

EXAMPLE 7

2 ml of 1,1,2-trichloroethane and 0.4 g of 1,1'-(m-phenylenedisulphonyl)-bis(4-n-butyl-2-tetrazolin-5-one) as prepared in example 6 were added to 2 ml of a 10% by weight solution in methylene chloride of the polyether obtained by polycondensation of epichlorohydrin and 2,2-bis(4-hydroxyphenyl)-propane. The solution was coated on an aluminium foil or on a non-subbed polyethylene terephthalate foil of 0.1 mm so that in both cases the dried layer had a thickness of 2 to 5 micron. This layer could be washed off easily with methylene chloride.

If the layer was heated for 5 to 10 minutes at 120° C, it could not be washed off any longer with methylene chloride, because as a result of the heating the 1,1'(m-phenylene-disulphonyl)-bis(4-N-butyl-2-tetrazolin-5-one) had decomposed and because these decomposition products immediately entered into reaction with the polyether and cross-linked the latter to the insoluble state.

EXAMPLE 8

0.04 g of 1,1'-(m-phenylene-disulphonyl)-bis(4-n-butyl-2-tetrazolin-5-one) was added to 4 ml of a 5% by weight solution in methylene chloride of low viscous polyvinylbutyraldehyde acetal, which comprised 20 mole % of recurring units with free hydroxyl groups). The solution was coated in the same way as described in example 7 on an aluminium foil or on a non-subbed polyethylene terephthalate foil having a thickness of 0.1 mm.

If the dried layers were heated for 5 to 10 minutes at 120° C, they could not be washed away any longer with methylene chloride.

EXAMPLE 9

1 ml of a 40% by weight aqueous carbon black dispersion was dispersed in the solution of polyether and 1,1'-(m-phenylene-disulphonyl)-bis(4-n-butyl-2-tetrazolin-5-one) as prepared in example 7. The resulting black coating composition was applied to a polyester foil. After having been dried, the resulting layer was exposed through a transparent line original by means of xenon gas discharge lamp placed at a distance of 10 cm. The discharge between the electrodes of the xenon gas discharge lamp produced a radiation energy of 610 watt. sec in 1/2000 sec. at a distance of 4 cm. At the exposed areas the light was converted into heat by the carbon black so that at these areas the polyether was cross-linked to the insoluble state.

After exposure the polyester foil was pressed with its polyether-tetrazolinon layer to a baryta-paper and gradually heated to 100° C, whereupon the polyester foil was stripped off. The exposed, hardened portions of the layer adhered to the polyester foil, whereas the unexposed and consequently non-hardened areas became sticky as a result of the heating and were thus transferred to the baryta paper. Upon heating above 100° C the polyether in the transferred areas was cross-linked to the insoluble state and in this way a positive relief image of the line original was formed.

We claim:

1. A compound of the formula:

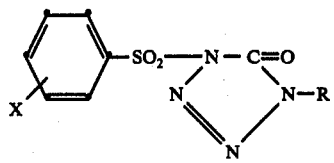

wherein:

X represents a hydrogen atom, a halogen atom, a nitro group, an alkyl group of 1 to 4 carbon atoms, or a group according to the formula:

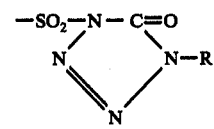

and R represents an aliphatic, aromatic or araliphatic hydrocarbon radical.

2. A compound of the formula:

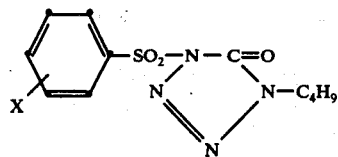
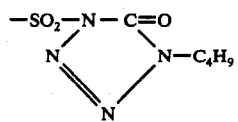
wherein X represents a hydrogen atom, a halogen atom, a nitro group, an alkyl group of 1 to 4 carbon atoms, or a group corresponding to the formula:
* * * * *